United States Patent [19]
Gottlieb

[11] Patent Number: 4,490,472
[45] Date of Patent: Dec. 25, 1984

[54] SENSITIVE TESTS FOR MALIGNANCIES BASED ON DNA DETECTION

[75] Inventor: A. Arthur Gottlieb, New Orleans, La.

[73] Assignee: Imreg, Inc., New Orleans, La.

[21] Appl. No.: 389,381

[22] Filed: Jun. 17, 1982

[51] Int. Cl.³ .................. C12N 15/00; C07H 15/12; G01N 33/50
[52] U.S. Cl. .................. 436/504; 436/804; 436/813; 436/815; 435/6; 435/172.3; 536/27; 935/19
[58] Field of Search ............... 424/1; 435/4, 6, 172.3, 435/253, 317, 174, 262, 270; 536/27–29; 252/301.1; 436/503, 504, 63, 64, 94, 804, 813, 815, 501, 503; 935/19

[56] References Cited

U.S. PATENT DOCUMENTS 4,358,535  11/1982  Falkow et al. .................. 435/5

*Primary Examiner*—Ben R. Padgett
*Assistant Examiner*—M. Moskowitz
*Attorney, Agent, or Firm*—Richard H. Stern

[57] ABSTRACT

An improved, more convenient, more sensitive test for detection of certain malignancies in human and animal subjects is disclosed. Sera from test subjects is mixed with labeled DNA in the presence of an enzyme-conjugated resin. Sera from normal and cancerous subjects react differently with the resin, permitting a diagnosis of the subject.

8 Claims, No Drawings

SENSITIVE TESTS FOR MALIGNANCIES BASED ON DNA DETECTION

BACKGROUND OF THE INVENTION

1. Field of the Invention

The present invention relates to improved means of testing human and animal subjects for the presence of certain malignancies. More specifically, an embodiment is disclosed that permits the diagnosis of several types of leukemia related to thymus cells, malignant B lymphocytes, and myelomas.

2. Detailed Discussion of Background and Prior Art

The inventor has discovered that blood sera and other body fluids collected from mice or human subjects with certain malignancies contain certain unique double-stranded DNA molecules, which have an affinity for certain members of the group of enzymes known as DNA polymerases. These DNA molecules are absent from sera obtained from mice or human subjects who do not have these malignancies. The inventor has, with others, described this discovery and these DNAs, with related information, in a series of papers. See: Perisco and Gottlieb, *DNA Polymerases of Myeloma*, Nature New Biology 239: 173–76 (1972); Gottlieb, Smith, Plescia, Persico, and Nicholson, *Inhibitor of DNA Polymerase*, Nature 246: 480–82 (1973); Gottlieb, Smith, Plescia, Nicholson, Bowers, Pankuch, and Berkoben, *An Inhibitor of DNA Polymerase*, in Fundamental Aspects of Neoplasia, ch. 20, pp. 269–77 (1975); Gottlieb, Gottlieb, and Nicholson, *Inhibition of DNA Polymerase by Sera*, in Bibliotheca Haematologica, No. 43 (Basel 1976); Brennessel, Buhrer, and Gottlieb, *Use of Insoluble Heparin for Isolation of DNA Polymerase*, Analytical Biochemistry 87: 411–17 (1978); Gottlieb, Chang, Buhrer, and Brennessel, *Isolation from Murine Myeloma and Leukemia Cells of a Selective Inhibitor of DNA Polymerase*, Cancer Research 40: 758–70 (1980).

The two DNA molecules of principal interest herein may be termed "DNA-1" and "DNA-2". It is believed that these DNAs may play an important role in the replication of leukemic cells. It is tentatively believed that DNA-1 is derived from and associated with malignant thymus cells, while DNA-2 is derived from and associated with malignant B lymphocytes and myeloma cells. DNA-1 and DNA-2 have important common properties and are at times hereafter referred to collectively as "DNA-L." (More precisely, "DNA-L" as used herein means a DNA selected from the group consisting of DNA-1 and DNA-2.)

Both DNA-1 and DNA-2 have been demonstrated to have an affinity for R-1 DNA polymerase enzyme, which is found in certain tumors. It may be recovered from murine MOPC-21 myeloma tumor by procedures described in Analytic Biochemistry 87: 411–17 (1978), supra.

Present tests for leukemia, such as bone marrow tests, may be inconvenient and traumatic for the patient. Also, their sensitivity is limited to detecting the presence of substantial numbers of cancer cells, so that early cases of leukemia may escape detection. The procedures of this invention do not involve production of antibodies, as in the work of Bogoch, Detection of Malignant Tumor Cells, U.S. Pat. No. 4,298,590 (Nov. 3, 1981). Such laborious and indirect methods of measurement are not used herein.

SUMMARY OF THE PRESENT INVENTION

The test procedure of this invention determines the presence of DNAs whose presence in body fluids in appreciable quantities is associated with malignant cells (hereafter "cancer DNAs") and thus the presence of malignant cells. It does so by subjecting a medium that possibly contains cancer DNAs to potential "competitive binding," the competitor being a known quantity of such a cancer DNA. The medium described below is blood serum, which the inventor prefers to use because of its convenience and accessibility, But other media, such as ascites fluid and lymph, also contain the cancer DNAs discussed herein and may contain other cancer DNAs of similar interest. Cerebrospinal fluid, duodenal fluid, gastric fluid, pleural fluid, urine, saliva, other mucous secretions, and other body fluids may also contain similar DNAs.

In the test described herein, the serum to be tested for a cancer DNA is mixed with a known quantity of "labeled" cancer DNA. The mixture is "introduced" to what is described below as an "Enzyme-Conjugated Matrix," which will bind with the cancer DNA but not with other kinds of DNA that may be present, or with other substances present. Then a test procedure is used to determine how much labeled DNA was taken up and bound to the Enzyme-Conjugated Matrix or left behind in the residue of the test mixture.

When relatively less labeled DNA is taken up by the Enzyme-Conjugated Matrix, the reason is that unlabeled similar DNA from the test serum competed for, and excluded the labeled DNA from, the enzyme sites on the Enzyme-Conjugated Matrix. When relatively more labeled DNA is taken up by the Enzyme-Conjugated Matrix, the reason is that unlabeled DNA similar to the labeled DNA was not present in the test serum to compete for, and thus exclude the labeled DNA from, the sites on the Enzyme-Conjugated Matrix.

A principal contribution of the present invention lies in the discovery of sensitive test procedures that permit early detection of leukemia or relapses, and that permit determination of whether a remission is in effect. These techniques, it is believed, are so sensitive as to detect the presence of as few as 250 malignant cells in a mouse or, by extrapolation on a blood and body weight basis, approximately 750,000 malignant cells in a human being. The latter figure may be contrasted with the approximately $4.5 \times 10^{10}$ cells present in the typical human blood stream, so that the test detects one part in approximately 60,000. Present leukemia tests, in contrast, are believed capable of detecting leukemia only when as many as approximately 10,000,000 malignant cells, or approximately 220 parts per million, are already established in the body.

There are several reasons why a more sensitive test is desired, that will permit earlier detection of malignancies such as leukemia. First, it is believed that earlier use of treatment will cause less harm to be done to the patient's body and possibly increase patient survival rates. But an early diagnosis is necessary before such therapy, which may be debilitating, is indicated. Second, leukemias are very alarming diseases. Mononucleosis is often confused with leukemia, because of similarity in symptoms. It is important to obtain a negative diagnosis of leukemia promptly in cases of mononucleosis, because of the severe adverse psychological effects on young patients and their parents of a diagnosis of possible leukemia.

The method of the invention is also cheaper, more convenient, less traumatic to the patient, more readily adaptable to large-scale screening, and more practical to use in frequent testing of the same patient—relative to existing procedures.

In the inventor's preferred usage, in this context, the term "leukemia" includes not only such leukemias as MCDV 12 and L 1211, but also myeloma. Accordingly, the following discussion and claims should be read in the light of such usage.

DETAILED DESCRIPTION OF PREFERRED EMBODIMENT

The test procedure of this invention is a new and improved means of testing for the presence of malignancies, such as leukemia, associated with particular DNAs. In the case of leukemia, the DNA is DNA-L. The inventor believes that other DNAs may exist, similarly related to other malignancies, and lending themselves to similar test procedures.

I. Preparation of Test Sample

The initial step in the inventor's leukemia test is to extract a quantity of blood (or other body fluid) from the test subject, remove cells by centrifugation to prepare serum (in the case of blood), and prepare a test sample from it. To do so, the fluid sample is treated with 70% ammonium sulfate to precipitate all protein in the sample. The precipitate is discarded and the supernatant fluid is retained. The latter is purified by centrifugation and dialysis. The resulting clear liquid is the test sample.

EXAMPLE 1

Test Sample 0.5 ml blood serum is obtained from a laboratory mouse. A saturated aqueous solution of ACS Reagent Grade $(NH_4)_2SO_4$ is added dropwise to the sample until a final concentration of 70% $(NH_4)_2SO_4$ is achieved. The resultant protein precipitate is removed by centrifugation at 17,000 g for 30 minutes, and is discarded. Approximately 1 ml of clear supernatant fluid is thus produced. It is dialyzed in a 12,000 M.W. dialysis sac against 0.01M Tris.HCl buffer (pH 7.8) overnight at 4° C. The material remaining in the dialysis sac (approximately 1 ml) is the test sample.

II. Preparation of Labeled DNA

The inventor has described generally the extraction of DNA-L in Cancer Research 40: 758 (1980), supra. It is possible to use a DNA-L mixture of DNA-1 and DNA-2 to perform the tests described here, but the inventor considers it scientifically unsound to do so, since that would require use of a product made up of DNA-1 and DNA-2 in unknown and variable proportions. The inventor has therefore developed a procedure for separating DNA-1 and DNA-2 from one another.

This procedure involves subjecting a human or murine test sample prepared as previously described in Example 1 and taken from a subject known to have leukemia, to sequential chromatography. The chromatography is performed on an Enzyme-Conjugated Matrix. This is an agarose-based, gel-like substance to which an enzyme can be covalently bound in a stable fashion, so that it is available for further use.

A general procedure is suggested for preparation of Enzyme-Conjugated Matrices in *Affinity Chromatography, Principles and Methods* (Pharmacia). The resin selected must be one to which the enzyme of interest will bind. The Pharmacia product, CNBr-Sepharose, has been found suitable for R-1 DNA polymerase, and the inventor has developed a procedure for preparing such a matrix. The inventor is aware of no published or otherwise previously known procedure for preparing an Enzyme-Conjugated Matrix in which R-1 DNA polymerase is bound to the matrix.

The following procedure differs from the general procedure cited above, in several important respects. The inventor has discovered that, to prepare an Enzyme-Conjugated Matrix effective for use in the procedures and tests described below, it is necessary to pretreat the Enzyme-Conjugated Matrix with buffer solution containing DNA, such as alkali-denatured salmon sperm DNA (Millipore Corp.). The matrix treated in this way is washed with buffer solution. If this pretreatment process with DNA is not carried out, the Enzyme-Conjugated Matrix will not react specifically with DNA-L.

EXAMPLE 2

Preparation of Purified Mixture of DNA-1 and DNA-2

A convenient volume (2 ml) of the test sample of Example 1 is prepared from pooled serum taken from inbred mice bearing myeloma MOPC-21. The dialysis step at the end of Example 1 is followed by concentration against 30% polyethylene glycol in 0.01M Tris.HCl buffer (pH 7.8). The resultant solution is further purified by chromatography on DEAE-cellulose (Whatman) using a linear KCl gradient of 0 to 1.0M in 0.01M Tris.HCl Buffer (pH 7.8). The DNA eluates at 0.45M KCl, and the eluted fractions are concentrated by dialysis against polyethylene glycol.

The resultant DNA preparation is adjusted to 0.4M in Sodium $PO_4$ buffer (pH 7.0), and heat-denatured by incubating for 16 minutes at 68° C. Distilled water is added to bring the phosphate concentration to 0.14M, and the mixture is placed on a 1 ml column of Hydroxylapatite (DNA grade, Bio-Rad Labs), which has been equilibrated in 0.01M Sodium $PO_4$ buffer (pH 7.0), boiled for 5 minutes, and maintained at 68° C. After placement of the DNA mixture on the column, the column is permitted to drain by gravity, and excess fluid is discarded. Then, 6.0 ml of 0.14M Sodium $PO_4$ buffer, (pH 7.0, 68° C.) is carefully layered on the column and drained.

The double-stranded DNA of interest is then released from the column by careful application of 8.0 ml of 0.4M Sodium $PO_4$ buffer (pH 7.0). The resultant preparation of a purified mixture of double-stranded DNA is referred to as "mixed DNA-L" or "DNA-L mixture."

EXAMPLE 2A

Similar Preparation (MCDV-12)

The procedure of Example 2 is repeated with mice bearing leukemia MCDV-12.

EXAMPLE 2B

Similar Preparation (L-1211)

The procedure of Example 2 is repeated with mice bearing leukemia L-1211.

EXAMPLE 2C

Similar Preparation (Pooled MOPC 21, MCDV-12, L-1211)

The procedure of Example 2 is repeated with pooled serum taken from mice bearing myeloma MOPC-21, leukemia MCDV-12, and leukemia L-1211, respectively, so that each leukemia is represented in the DNA-L mixture.

Separation of DNA-1 and DNA-2 is achieved by fractionation of mixed DNA-L on an Enzyme-Conjugated Matrix. This is an insoluble Sepharose (Pharmacia) matrix to which R-1 DNA polymerase is covalently attached. It is prepared on the general basis, somewhat varied to meet the particular needs of this situation, of the method described in *Affinity Chromatography—Principles and Methods* (Pharmacia), which is based on the original method of Axen, Porath, and Ernback, *Chemical Coupling of Peptides and Proteins to Polysaccharides by Means of Cyanogen Halides*, Nature 214: 1302–04 (1967). Other insoluble matrices may be used instead of affinity matrices such as Sepharose, described below. For example, it is known to use glass beads, ceramics, and silica to provide a support for enzymes in enzymatic processes. The Enzyme-Conjugated Matrix must also be pretreated to bind specifically with DNA-L, as described below.

EXAMPLE 3

Preparation of Enzyme-Conjugated Matrix 1 gram of CNBr-activated Sepharose 4B (Pharmacia) is swollen in 0.001M HCl on a glass filter and washed for 15 minutes with 200 ml of 0.001M HCL. The resulting gel is washed with 0.1M $NaHCO_3$ (pH 8.3) and then with 0.1M $NaHCO_3$ (pH 8.3) containing 0.5M NaCl. The gel is then suspended in 3.5 ml of the latter buffer. Purified R-1 DNA polymerase (containing approximately 0.040 mg of protein in 1.0 ml of 0.28M Potassium $PO_4$ buffer (pH 6.3) with 0.001M DTT (dithiothreitol) and 20% glycerol) is added to the gel slurry, and the mixture is shaken on a wrist action shaker overnight at 4° C.

The gel is then washed twice with 0.1M $NaHCO_3$ containing 0.5M NaCl (pH 8.3), prior to blocking the remaining active groups with 1M Tris.Hcl buffer (pH 8.0) for 2 hours at room temperature. Three cycles of washing the gel follow: each cycle consists of a wash with 0.1M acetate buffer containing 1M NaCl (pH 4.0) and is followed by a wash with 0.1M borate buffer containing 1M NaCl (pH 8.0).

The Sepharose gel containing the R-1 DNA polymerase, prepared in this manner, is then suspended in "Buffer-A" (0.054M Tris.HCl (pH 7.8), containing 0.005M 2-mercaptoethanol, 0.0001M $MnCl_2$, 0.04M KCL). A 1 ml minicolumn is then poured. The Enzyme-Conjugated Matrix is now ready for use. It may also be stored, and remains in good condition when stored at 4° C. for up to at least 3 months.

The inventor has found that DNA-L binds specifically to the Enzyme-Conjugated Matrix only when the latter is pretreated. It is therefore important to include such pretreatment of the Enzyme-Conjugated Matrix as part of the procedure followed herein. It is believed that use of such procedure in connection with such matrices is unknown in the prior art.

EXAMPLE 4

Pretreatment of Column

The column of Example 3 is pretreated with 5 ml of a conveniently available nonhuman, nonmurine DNA, such as alkali-denatured salmon sperm DNA (50 micrograms/ml) which is passed through the column at 4° C. The column is then washed sequentially with 10 ml of Buffer-A, 10 ml of Buffer-A plus 0.5M KCl, and 10 ml of Buffer-A again.

EXAMPLE 5

Separation of DNA-1 and DNA-2

The preparation of mixed DNA-L of Example 2 (a purified mixture of DNA-1 and DNA-2) is passed through the column of Examples 3 and 4, and the eluate is recycled through the column over a 20-minute period.

The column is then drained and washed again with 5 ml of Buffer-A (Example 3), which is followed by elution of the DNA-L mixture with 5 ml of a linear gradient of KCl (0–1M in Buffer-A). DNA-1 elutes at 0.1M KCl; DNA-2 elutes at 0.22M KCl. Following completion of the gradient, the column is washed with 5 ml of Buffer-A containing 1M KCl. (The column can be regenerated for further use by washing with 15 ml of Buffer-A.)

Of the original input DNA, approximately 4.5% is recovered as DNA-1 and 4.6% as DNA-2.

Separation of DNA-1 and DNA-2 permits preparation of a pure, cloned DNA-1 or DNA-2 for test purposes. It is possible to use a purified mixture of natural DNA-L extracted from a living source for these tests, but the inventor prefers to use a pure, cloned product. It is cheaper and more convenient, once the procedure is established. It is also believed to be scientifically more sound, since it elimates a possible variable factor, i.e., the presence of contaminating DNAs in the DNA-L preparation.

The inventor has therefore used a cloning procedure employing the pBR322 plasmid as cloning vector. The following example refers to DNA-1, but the procedure for cloning DNA-2 is substantially identical. The general approach used here is based on the method described in Bahl, Marians, Wu, Stawinsky, and Narang, *A General Method For Inserting Specific DNA Sequences Into Cloning Vehicles*, Gene 1: 81–92 (1976). The method uses "linkers" sensitive to the restriction enzyme Bam I as described in Scheller, Dickerson, Boyer, Riggs, and Itakura, *Chemical Synthesis of Restriction Enzyme Recognition Sites Useful for Cloning*, Science 196: 177–80 (1977). Alternatively, the cloning method employing the single-stranded M13 phaze, as described by Sanger, Coulson, Barrell, Smith and Roe, J. Molecular Biology (1980) 143: 161–178, may be employed.

Before cloning the DNA-1, it is desirable, however, to "label" it to facilitate parts of the cloning procedure. Both the cloning and the malignancy test procedures described below require use of "labeled" DNA. That is DNA that is physically or chemically treated, so that it can be followed and measured through subsequent procedures. Typically, radioactive material is used to label molecules for such purposes. The inventor has found that phosphorous 32 ($32_P$) and tritum are particularly useful and effective isotopes for labeling DNA-L. While radioactive labeling is described below, it is known in the art to use optically active labels such as dyes or fluorescent complexes and to use radio-opaque agents, to assist in visualizing the thus-labeled substance; and it is intended to include within the concept of labeling (as subsequently claimed) all such equivalent means.

Further, the labeled DNA used for competitive binding may be a modified cancer DNA selected for its affinity with the enzyme to which the natural cancer DNA of the test binds; in such event, the modified DNA can be used in lieu of naturally-derived DNA for the labeled DNA of the test.

A radioactive label is inserted into the DNA molecule by an enzymatic process, as described below. The following example refers to DNA-1 but the procedure for DNA-2 is substantially identical. The term "DNAse I" used below refers to a bacterial enzyme capable of introducing single strand breaks or gaps in double-stranded DNA molecules. The DNAse I enzyme used here is that obtained from Millipore Corp., but there are other suppliers.

EXAMPLE 6

Labeling DNA-1

The following are mixed in 2 microliters of a 0.005M Tris.HCl buffer (pH 7.4): 180 pmoles of radio-labeled ($32_p$) deoxynucleoside triphosphates; 1.8 microliters of each of four unlabeled deoxynucleoside triphosphates (known in the art as dCTP, dATP, dGTP, and TTP); 10 microliters of 10 X reaction buffer; and 2 micrograms of the DNA-1 of Example 5. After mixing, distilled water is added to bring total volume to 94 microliters. This mixture is referred to as "Labeling Mixture."

"Activation buffer" is prepared by mixing 10 ml Tris.HCl (pH 7.6); 0.005M $MgCl_2$; and 1 mg/ml nuclease-free BSA. 9 microliters of Activation Buffer is mixed with 1 microliter of a solution containing 100 micrograms/ml of DNAse I (equivalent to 0.1 microgram DNAse I), and the mixture is let sit at 4° C. for 2 hours. This mixture is referred to as "Activated DNAse I."

One microliter of Activated DNAse I is added to 9.6 microliters of Labeling Mixture, and the resulting mixture is incubated for 10 minutes at 15° C. To that mixture is then added two units of E. Coli DNA polymerase I (1 Unit/microliter) in 2 microliters of Potassium $PO_4$ (pH 7.0) buffer. The buffer contains 1 millimeter of 2-mercapthoethanol and 50 percent glycerol. The reaction is continued for one hour, and is stopped by addition of 0.2 ml of 0.3M $Na_2EDTA$ (pH 8.0). The DNA is then separated from residual nucleotides by chromatography on a column of Sephadex G-50 (fine grade) (Pharmacia) previously equilibrated in a suitable volume of 0.01M Tris.HCl containing 0.0001M $Na_2EDTA$ (pH 8.0).

EXAMPLE 7

Cloning DNA-1

Phosphorylation buffer (10X) is prepared, consisting of 0.7M Tris.HCl (pH 7.6) and 0.1M $MgCl_2$. 1 microliter of the buffer is mixed with 0.5 microliter of 0.01M ATP, 5 microliters of 0.01M DTT, 1 microliter of 4.5 micrograms/microliter T4 Polynucleotide Kinase (New England Biolabs). Then, 500 ng of Bam linker, dissolved in 1 microliter of water, is added. Further water is added to bring volume up to 10 microliters. The mixture is incubated for 1 hour at 37° C., and is then frozen at −20° C. for storage. This mixture is referred to as "phosphorylated Bam linker" or "PBM".

A mixture is prepared containing 10 Units of T4 DNA Ligase (New England Biolabs) in 82 microliters of 0.07M Tris.HCl (pH 7.5), containing 0.007M $MgCl_2$ and 70 micro M ATP. To this is added 10 micrograms of the labeled DNA-1 of Example 6 and 1.8 micrograms of PBM in 18 microliters of water. The resulting 100 microliters of mixture is incubated at 15° C. overnight and the reaction is stopped by bridging the temperature of the mixture to 65° for 10 minutes. This produces a mixture containing DNA-linker molecule.

To the mixture is then added 100 Units of Bam HI in 10 microliters of water and 12 microliters of Bam 10X buffer (0.2M Tris.HCl (pH 8.0), 0.07M $MgCl_2$, 0.02M BME, 1M NaCl). The mixture is incubated at 37° C. for 3 hours, and the reaction is stopped by adding 12 microliters of 0.2M $Na_2EDTA$. This trims the PBM from the DNA-linker molecule.

The DNA-linker mixture is sequentially treated with phenol and ether to extract DNA-linker from it. The volume of the extract is reduced to 20 microliters by passing nitrogen gas over it.

The concentrated extract is passed over a 1 ml column of Sephadex G-50 (Pharmacia) equilibrated in 0.01M Tris.HCl (pH 7.8) containing 0.05M NaCl. One drop fractions are collected in microfuge tubes. The location of the DNA-linker is determined by detection of the $32_p$ label, and the volume of the solution containing DNA-linker is measured (approximately 0.1 ml). The DNA-linker is recovered by addition of 10 microliters of 3M Na Acetate and 0.2 ml of ethanol. The mixture is allowed to stand at −20° C. overnight.

The precipitated DNA-linker is then pelleted by centrifugation and dried in vacuum. The pellets are dissolved in 30 microliters of water and stored at −20° C.

1 microgram of pBR322 (BRL Labs) is treated with BAM I and bacterial alkaline phosphatase and placed in a volume of 5 microliters of water. To this is added 2 microliters of IOX Ligase buffer (20 Units T4 DNA Ligase in 2 microliters) and 1 microgram of DNA-linker pellets in 2 microliters of water. Volume is adjusted to 20 microliters by addition of water. The mixture is incubated at 15° C. overnight. As a result, the DNA-linker is now ligated into the pBR322 plasmid vector, and the mixture contains DNA-linker-pBR322 vector.

HB101 E. coli is then infected with the DNA-linker-pBR322 vector. Host HB101 cells are pretreated with chilled 0.1M $CaCl_2$ and are incubated at 4° C. for 15 minutes, and are recovered by centrifugation. To 0.3 ml of cell pellet are added 100 mg of the vector. The E. coli/vector mixture is placed in ice for 10 minutes and is then given a 30 second thermal shock at 37° C. The E. coli/vector mixture is then incubated on ice for 90 minutes.

A "ML medium" mixture is prepared of 1% Bactopeptone, 0.5% yeast extract, and 0.5% NaCl. Then, 2 ml of ML medium is added to the E. coli/vector mixture, and the mixture is incubated at 37° C. for 60 minutes. Ampicillin is added to the mixture to bring about a concentration of 40 micrograms/ml and incubation is continued at 37° C. for 30 minutes.

0.5 ml of the mixture is plated on ML medium containing 50 micrograms/ml of Ampicillin. A separate plating is made using a 1:10 dilution of the mixture. The plates are incubated overnight at 37° C. The number of colonies is counted.

Replica plates are then made on ampicillin and tetracycline. The E. coli colonies of interest are those that have lost resistance to tetracyline and retained resistance to ampicillin. Approximately 5 to 10 colonies survive out of about 300 that are found on the original ampicillin-containing plates.

Each E. coli colony is grown separately in 10 ml ML medium for 7 hours at 37° C. Chloramphenicol is then added to reach a concentration of 100 micrograms/ml and incubation is continued at 37° C. overnight. The solutions are pooled and centrifuged to recover cell pellet. The pellet is taken up in 0.7 ml of STET buffer (0.05M Tris.HCl (pH 8.0), containing 8% sucrose, 5% Triton-X-100, 0.5M EDTA) to which 50 microliters of lysozyme (10 mg/ml) is added.

The mixture is centrifuged immediately at 12,000 g for 10 minutes at room temperature. The resulting supernatant is placed in microfuge tubes. An equal volume (approximately 0.4 ml) of isopropanol is added and the mixture is placed at $-20°$ for 1 hour and then centrifuged.

The resulting DNA pellet is washed with ethanol, resuspended in 0.5 ml buffer (0.02M Tris.HCl (pH 8.1), containing 0.01M EDTA, 0.1M NaCl) and treated with RNAse-A (Millipore), RNAse T1 (Sigma), and Proteinase K (EM Biochemicals, Darmstadt) to respective final concentrations of 100 micrograms/ml, 25 U/ml, and 0.025 mg/ml for 5 hours at 37° C.

The mixture is then extracted with 0.5 ml of buffer saturated phenol and shaken for 5 minutes and extracted with chlorform (0.166 ml) for 5 minutes. The resultant aqueous phase is extracted with ether to remove phenol and chloroform. 0.05 ml of 3M Na Acetate is added to the aqueous phase, and then 2 volumes of cold ethanol follow. The mixture is held overnight at $-20°$ C.

The precipitated DNA is washed with ethanol, vacuum dried, and resuspended in a suitable volume (approximately 100 ml) of 0.005M Tris.HCl (pH 7.4) containing 0.0001M EDTA.

A sample of the DNA is tested and its ability to inhibit R-1 DNA polymerase confirms its identity.

III. Preparation of Enzyme-Conjugated Matrix for Tests

There may be a number of enzymes with an affinity for (i.e., capable of binding to) DNA-L. Although the inventor has thus far found only one that is effective in these tests, it is believed that trial and error procedures could develop others useful in these tests on the basis of the techniques described herein, and they are considered within the scope of this invention. The enzyme used here is R-1 DNA polymerase, extracted by the procedure described in Analytic Biochemistry 87: 411 (1978), supra. The inventor has tested R-1 DNA Polymerase with samples of other DNAs that may be present in blood and other body fluids, and found that none of those DNAs appeared to specifically inhibit the R-1 DNA polmerase.

EXAMPLE 8

Preparation of Enzyme-Conjugated Matrix for Tests

The procedure of Example 3 is carried out, using the same CNBr-activated-Sepharose. The pretreatment procedure of Example 4 is carried out.

The resulting product is an R-1 DNA polymerase Enzyme-Conjugated Matrix suitable for use in the tests described herein. It remains stable at 4° C. for at least 3 months. It may be regenerated for repeated use by washing with 1M KCl followed by assay buffer.

IV. Test Procedure

As already indicated, the invention detects presence of cancer DNA (DNA whose production in appreciable quantity is associated with malignancies) by means of "competitive binding." Labeled DNA "competes" with any cancer DNA occurring in the test subject's blood (or other body fluid) for binding sites on the enzyme in the Enzyme-Conjugated Matrix. The proportion of labeled DNA taken up and bound to the Enzyme-Conjugated Matrix is related to the presence or absence of competing DNA in the test subject's blood (or fluid). If no competitive DNA is present, a maximum amount of labeled DNA is bound to the Enzyme-Conjugated Matrix. But if competitive DNA is present, a lesser amount of labeled DNA is bound to the Enzyme-Conjugated Matrix. The proportion of labeled DNA bound to the Enzyme-Conjugated Matrix under these conditions is thus an indicator of the presence of cancer DNA in the test subject's blood or fluid.

The test procedure involves the steps of preparing a test sample from the test subject's blood or fluid (Example 1); mixing labeled DNA-1 (Example 6), preferably cloned (Example 7) rather than natural, with the sample; "introducing" the test sample containing labeled DNA ("DNA/sample mixture") to an Enzyme-Conjugated Matrix (Example 8); and, finally, determining how much labeled DNA has become bound to the Enzyme-Conjugated Matrix.

To "introduce" the DNA/sample mixture to the Enzyme-Conjugated Matrix, a known quantity of the DNA/sample mixture is mixed with buffer and a known quantity of the Enzyme-Conjugated Matrix of Example 8. The latter contains a known quantity of enzyme. The resulting mixture is then incubated for 15 minutes at 25° C. The matrix is then separated from the fluid residue of the DNA/sample mixture and buffer, by centrifugation. To obtain best results, the relative concentrations of labeled DNA and Enzyme-Conjugated Matrix should have a relationship such that, at anticipated concentrations of the cancer DNAs of interest (which, in the case of leukemia, is DNA-L) in the test serum, there is a considerable difference (e.g., 10% versus 90%) between the results of a test on a normal blood sample and one on a "malignant" blood sample.

The inventor believes that 1 molecule of DNA binds to 1 molecule of enzyme, and that the molecular weight of the DNA-L is approximately equal to the molecular weight of the R-1 DNA polymerase enzyme, so that 1 nanogram of pure DNA-L and 1 nanogram of pure enzyme each represent the same number of molecules (i.e., of DNA-L or enzyme, respectively). The examples that follow are described in terms of both purified DNA-L and preparations of R-1 DNA polymerase enzyme purified to homogeneity. Using purified DNA-L presents no serious technical problem, when procedures such as those already described are used. But purification of the enzyme preparation to homogeneity presents technical difficulties. It may therefore be desirable to use non-homogeneous enzyme preparations, instead. This, of course, requires that larger amounts of these enzyme preparations be conjugated to the matrix in order to provide a sufficient number of enzyme molecules on the surface of the matrix. (E.g., a 95% pure enzyme preparation requires use of approximately 105% the amount of enzyme preparation, and so on.) The inventor believes that the impurities present in the enzyme preparation do not affect the binding or inhibition of the enzyme by DNA-L.

There are at least two ways to test for take-up of labeled DNA. One is to test the residual fluid that remains after the removal of the Enzyme-Conjugated Matrix. If x percent of labeled DNA remains in the residual fluid, 100-x percent was bound to the Enzyme-Conjugated Matrix. The other way is to test the Enzyme-Conjugated Matrix, by extracting from it substantially all of the bound, labeled DNA and measuring the latter. Ideally, the two methods are complementary, and the sum of the two amounts of labeled DNA (in the residual fluid and in the Enzyme-Conjugated Matrix) should be equal to the amount of labeled DNA and added to the test serum.

Unfortunately, this does not occur, due to experimental error. The first method, the residual fluid assay method, is believed to be almost 100 percent accurate. The second method, the matrix assay method, involves losses in washing, inadequate extraction, etc., that are believed to amount to about 25%. This estimate is based on the inventor's tests using a test serum with 100% labeled DNA-L, the DNA-L being present in excess of the available sites, so that about 50% would be in each moiety; performing both assay methods; and attributing all loss to the matrix assay method.

The preferred embodiment, at least for DNA-L and the leukemia test, is therefore the residual fluid assay method, rather than the matrix assay method, although the latter is a check on the former. It may also be noted that the procedures of the matrix assay method are more laborious and time-consuming than those of the residual fluid assay method.

The following examples all refer to DNA-1. In all respects known to the inventor, DNA-2 produces identical results to DNA-1, and it makes no difference which is used. Also, no difference is found between the results of tests using cloned DNA-L originally obtained, respectively, from humans or mice, although human and mouse DNA-L are believed not to be identical.

EXAMPLE 9

Test of Normal Mouse (Residual Fluid Assay Method)

1.0 cc of serum is obtained from a laboratory mouse believed to be normal. Test sample is prepared in accordance with Example 1.

To 0.5 cc of the test sample, 0.5 cc is added of an aqueous buffered mixture containing the labeled DNA-1 solution of Example 6. The DNA solution contains 2.0 micrograms/cc of the pure, labeled, cloned DNA-1 of Example 7, or a total of 1.0 microgram. The solutions are thoroughly mixed, and the resulting DNA/sample mixture is then ready for "introduction" to the Enzyme-Conjugated Matrix.

0.5 ml of a suspension of the Enzyme-Conjugated Matrix containing approximately 1 micrograms of pure R-1 DNA polymerase enzyme is added to the DNA/sample mixture. After incubation at 25° C. for 15 minutes, the matrix is recovered by centrifugation, and put aside.

The residual fluid is collected. It is tested for labeled DNA-1 by liquid scintillation spectrometry. It is found that the residual fluid contains 0.16 micrograms of labeled DNA-1. This is 16% of the amount originally in the DNA/sample mixture.

The mouse is kept alive for 30 days and is then sacrificed, at which time it shows no signs of malignancy.

EXAMPLE 10

Test of Normal Mouse (Matrix Assay Method)

The test of Example 9 is repeated, but the assay is performed on the matrix by liquid scintillation spectrometry.

It is found that the matrix has bound to it 0.56 micrograms of labeled DNA-1. This is 56% of the amount originally in the DNA/serum mixture.

EXAMPLE 11

Test of Mouse With Known Leukemia

The procedure of paragraphs 1 through 3 of Example 9 are repeated with a laboratory mouse known to have multiple myeloma. The residual fluid assay method is used.

It is found that the residual fluid contains 0.82 micrograms of labeled DNA-1. This is 82% of the amount originally in the DNA/sample mixture. The ratio of this percentage to that of Example 9 (normal mouse) is approximately 5.1 to 1.

The mouse is sacrificed. Examination at autopsy reveals typical signs of myeloma.

To demonstrate the sensitivity of the test method, for use in early detection of small colonies of leukemia cells, a diluted leukemia sample may be prepared. A sample of test serum from the mouse of Example 11 is therefore diluted with a test sample from the normal mouse of Example 9, in the ratio 1:500. The prior test procedure is varied to account for the lesser amount of DNA-L anticipated to be present.

EXAMPLE 12

Dilution Test of Mouse With Known Leukemia

The test procedures of Example 9 are followed on the diluted test sample. To 0.5 cc of the diluted test sample is added 0.5 cc of an aqueous buffered mixture containing 2.0 micrograms/cc of the pure, labeled, cloned DNA-1 of example 7, i.e., a total of 1.0 microgram. The use of the residual fluid assay method indicates that the residual fluid contains 0.59 micrograms of labeled DNA, which is 59% of the original amount.

The same test is repeated with the unmixed "normal" test serum of Example 9. The use of the residual fluid assay method indicates that the residual fluid contains 0.18 microgram of labeled DNA-1, which is 18% of the original amount. The ratio of the two percentages is 3.3 to 1.

The foregoing procedures provide an entirely new diagnostic method, hitherto unknown to medical science. It is believed significant that these procedures use pure, laboratory-produced reactants (such as cloned DNA) rather than substances that must be obtained from donors and then be purified. The procedures described above utilize DNA-L (the DNAs referred to as DNA-1 and DNA-2), but the inventor believes that other DNAs associated with other malignancies (e.g., that of the lymph system) will be isolated and be found useful in tests that are slight variations of the tests described above, and accomplish the same type of result in the same way.

Moreover, other resin matrices may be utilized, and so too may polystyrene and latex beads, to which the enzyme may be chemically bonded. Examples of the latter are carboxylated monodisperse "microspheres" (marketed by Polysciences Inc., Washington, Pa.) and hydrophilic latex spheres ("Covaspheres "MX" or "FX," Covalent Technology Corp., Ann Arbor, Mich.). Also, other enzymes having an affinity with (i.e., capable of binding to) the pertinent DNA may be utilized.

While the invention has been described primarily in connection with a specific and preferred embodiment thereof, it will be understood that it is capable of further modifications without departing from the spirit and scope thereof. Some such modifications are described above. This application is intended to cover all variations, uses, or adaptations of the invention, following, in general, the principles of the invention and including such departures from the present disclosure as come within known or customary practice within the art to which the invention pertains.

What is claimed and desired to be secured by United States Letters Patent is:

1. Substantially pure DNA-L, substantially free of other DNAs.
2. The DNA-L of claim 1, wherein said DNA-L is labeled DNA-L.
3. The DNA-L of claim 1, wherein said DNA-L is cloned DNA-L.
4. The DNA-L of claim 3 wherein said DNA-L is labeled DNA-L.
5. The DNA-L of claim 2 wherein said labeled DNA-L is labeled with a member of the group consisting of phosphorous 32 and tritium.
6. The DNA-L of claim 3 wherein said DNA-L is DNA-1.
7. The DNA-L of claim 3 wherein said DNA-L is DNA-2.
8. A substantially pure, labeled mixture of DNA-1 and DNA-2, substantially free of other DNAs.

* * * * *